(12) United States Patent
Cho

(10) Patent No.: US 9,176,097 B2
(45) Date of Patent: Nov. 3, 2015

(54) WELDED PORTION QUALITY DETERMINING SYSTEM

(71) Applicant: Hyundai Motor Company, Seoul (KR)

(72) Inventor: Yong Joon Cho, Yongin-si (KR)

(73) Assignee: HYUNDAI MOTOR COMPANY, Seoul (KR)

( * ) Notice: Subject to any disclaimer, the term of this patent is extended or adjusted under 35 U.S.C. 154(b) by 91 days.

(21) Appl. No.: 14/038,693

(22) Filed: Sep. 26, 2013

(65) Prior Publication Data

US 2014/0167747 A1    Jun. 19, 2014

(30) Foreign Application Priority Data

Dec. 17, 2012   (KR) .......................... 10-2012-0147770

(51) Int. Cl.
*G01N 27/72* (2006.01)
*B23K 11/31* (2006.01)
*G01N 27/82* (2006.01)

(52) U.S. Cl.
CPC ...................................... *G01N 27/82* (2013.01)

(58) Field of Classification Search
CPC ...................................................... G01N 27/82
USPC ........................................................... 324/226
See application file for complete search history.

(56) References Cited

FOREIGN PATENT DOCUMENTS

JP          2011034731  A  *  2/2011
KR          20-0281248  Y       6/2002

OTHER PUBLICATIONS

Partial Machine Translation of JP2011034731A, Feb. 2011.*

* cited by examiner

*Primary Examiner* — Bot Ledynh
(74) *Attorney, Agent, or Firm* — McDermott Will & Emery LLP

(57) ABSTRACT

A welded portion quality determining system includes a first plate and a second plate, a welded portion defined at a point where the first plate and the second plate are welded to each other. Magnetic field generators generate a magnetic field to be supplied to the welded portion, and magnetic pickup devices receive the magnetic field generated by the magnetized welded portion to sense the received magnetic field. Therefore, a magnetic field may be generated by the welded portion through the magnetic field generators, and the magnetic field generated by the magnetized welded portion is sensed by the magnetic pickup devices so that quality of the welded portion may be rapidly and correctly verified.

5 Claims, 8 Drawing Sheets

WELDED PORTION QUALITY DETERMINING SYSTEM

CROSS-REFERENCE TO RELATED APPLICATION

This application claims the benefit of priority to Korean Patent Application No. 10-2012-0147770 filed in the Korean Intellectual Property Office on Dec. 17, 2012, the entire contents of which are incorporated herein by reference.

TECHNICAL FIELD

The present disclosure relates to a welded portion quality determining system for determining quality of a welded portion in which two parts are welded to each other to improve quality and durability of a product.

BACKGROUND

In general, a production line of a vehicle body includes a welding process. When a plate such as a vehicle body panel is welded, a weldment is applied into a space between electrodes with pressure and current so that a pressed portion is fused by electric resistance heating of a contact portion.

In order to satisfy increasing demand of assembly quality of a vehicle body, welding quality needs to be improved. However, it is difficult to guarantee the welding quality solely by monitoring a welding machine. Therefore, ultrasonic testing is representatively used for checking the welding quality after the vehicle body is welded.

FIG. 1 is a cross-sectional view of a conventional welded portion quality determining system using ultrasonic waves. The conventional welded portion quality determining system includes an ultrasonic wave generator 100, a housing 110, a medium 120, and a layer 130.

In the ultrasonic testing for testing welding quality of a resistance point according to the related art, a liquid transmission medium is coated on a surface of an object to be tested. Since intensity of ultrasonic waves with respect to a time axis is represented as a pulse type graph in the ultrasonic testing result, the graph may not be easily comprehended with basic knowledge.

One with comprehensive reading technology manually brings an ultrasonic probe into contact with a surface of a welded portion coated with the liquid medium and reads the graph to determine quality of the welded portion.

As described above, due to the manual processes of coating the liquid medium and reading the graph, it is difficult to quantify the test result of the welding quality of the welded portion of the vehicle body using the conventional ultrasonic testing, and it is difficult to correctly test the welding quality.

The above information disclosed in this Background section is only for enhancement of understanding of the background of the disclosure, and therefore it may contain information that does not form the prior art that is already known in this country to a person of ordinary skill in the art.

SUMMARY

An aspect of the present disclosure provides a welded portion quality determining system, in which quality may be quantified unlike in a conventional art, for determining the welded portion quality to improve durability of a product.

A welded portion quality determining system according to an exemplary embodiment of the present disclosure may include a first plate and a second plate, a welded portion defined at a point where the first plate and the second plate are welded to each other. Magnetic field generators generate a magnetic field to be supplied to the welded portion, and magnetic pickup devices receive the magnetic field generated by the magnetized welded portion to sense the received magnetic field.

A magnetic camera may include the magnetic field generators and the magnetic pickup devices. One surface of the magnetic camera may be disposed near one surface of the first plate or the second plate.

The magnetic field generators may be arranged at predetermined intervals in horizontal and vertical directions.

The magnetic field generators may be sequentially operated in the horizontal or vertical direction in the order of arrangement to generate the magnetic field.

The magnetic pickup devices may be arranged at predetermined intervals in the horizontal and vertical directions.

The magnetic pickup device corresponding to the operated magnetic field generator among the magnetic field generators may be operated to sense the magnetic field generated by the welded portion.

The welded portion quality determining system may further include a storage for storing first information on a magnetic field generated by a normal welded portion irradiated by the magnetic field to be magnetized and second information on a magnetic field generated by an abnormal welded portion irradiated by the magnetic field to be magnetized. An operator compares third information on the magnetic field generated by the magnetic pickup devices with the first and second information. A controller determines a state of the welded portion using an operation result from the operator.

As described above, in the welded portion quality determining system according to an exemplary embodiment of the present disclosure, the magnetic field may be generated by the welded portion through the magnetic field generators. The magnetic field generated by the magnetized welded portion is sensed by the magnetic pickup devices so that quality of the welded portion may be rapidly and correctly verified.

DETAILED DESCRIPTION

An exemplary embodiment of the present disclosure will hereinafter be described in detail with reference to the accompanying drawings.

Figure 1:
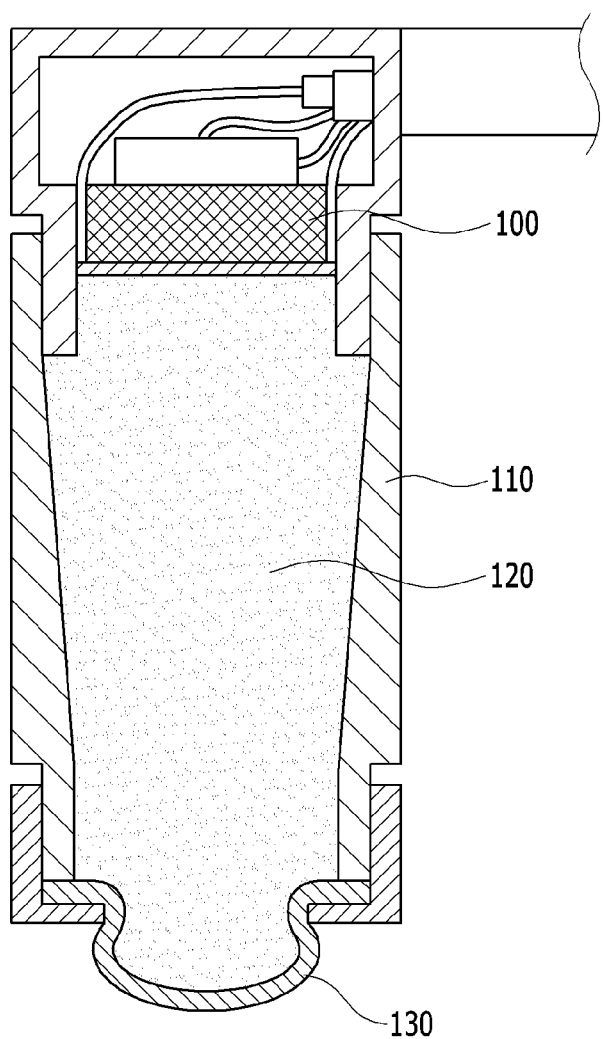
FIG. 1 is a cross-sectional view of a conventional welded portion quality determining system using ultrasonic waves.
Figure 2:
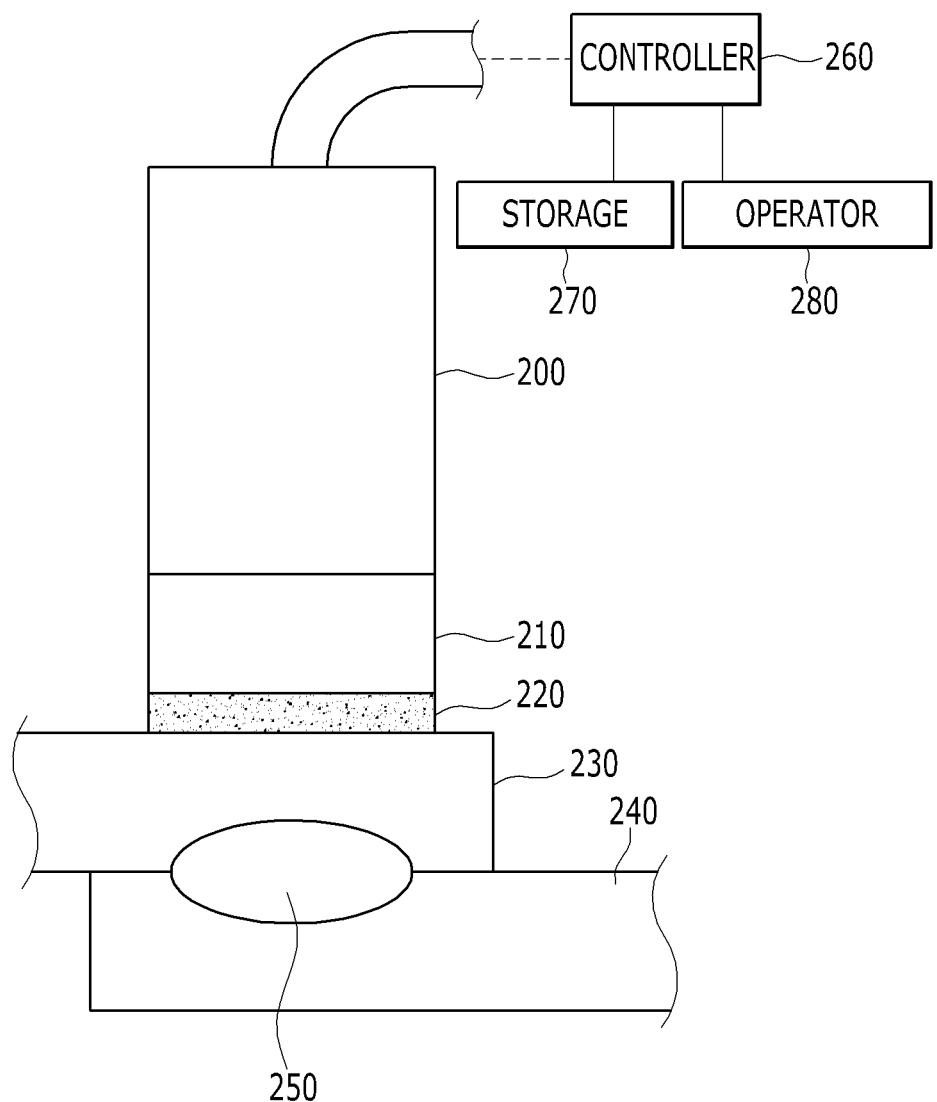
FIG. 2 is a schematic block diagram of a welded portion quality determining system according to an exemplary embodiment of the present disclosure.

FIG. 2 is a schematic block diagram of a welded portion quality determining system according to an exemplary embodiment of the present disclosure.

Referring to FIG. 2, a welded portion quality determining system includes a controller 260, a storage 270, an operator 280, a body 200, a magnetic camera 210, a rubber 220, a first plate 230, a second plate 240, and a welded portion 250.

The body 200 supplies power to the magnetic camera 210 and electrically connects the controller 260 and the magnetic camera 210 to each other.

The magnetic camera 210 generates a magnetic field to be supplied to a welded portion 250, picks up or senses the magnetic field generated by the welded portion 250, and transmits a sensed signal to the controller 260.

The controller 260 datarizes the sensed signal by the operator 280, compares data obtained by datarizing the sensed signal with data stored in the storage 270, and determines quality of the welded portion 250.

Pickup magnetic field data generated by a normal welded portion and an abnormal welded portion are stored previously in the storage 270.

Figure 3:
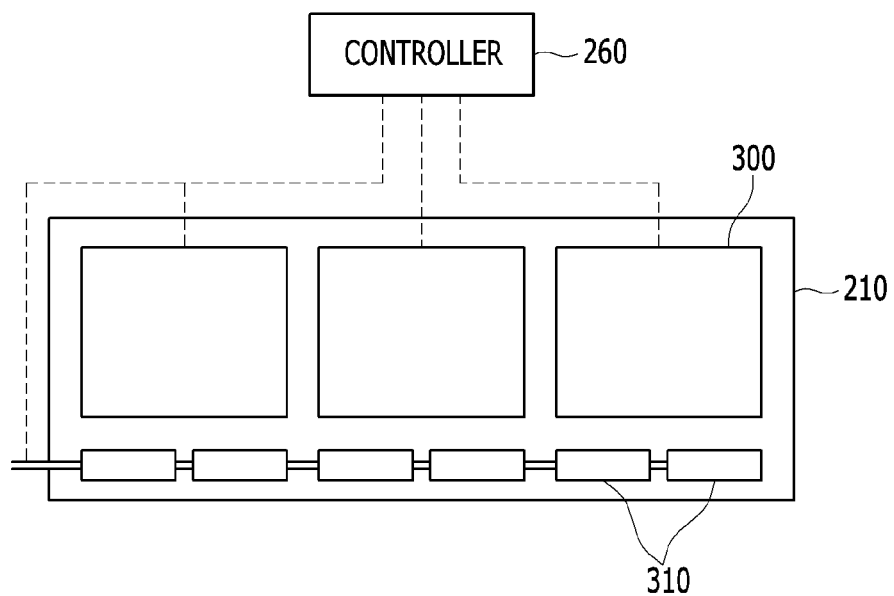
FIG. 3 is a schematic block diagram of a magnetic camera in a welded portion quality determining system according to an exemplary embodiment of the present disclosure.

FIG. 3 is a schematic block diagram of a magnetic camera in a welded portion quality determining system according to an exemplary embodiment of the present disclosure.

Referring to FIG. 3, the magnetic camera 210 includes magnetic field generators 300 and magnetic pickup devices 310. The magnetic field generators 300 generate the magnetic field to be supplied to the welded portion 250 using power supplied from a power generator (not shown).

The welded portion is magnetized by the magnetic field generated by the magnetic field generators. The magnetic pickup devices 310 sense the magnetic field generated by the magnetized welded portion 250 and transmit the sensed signal to the controller 260.

Figure 4:
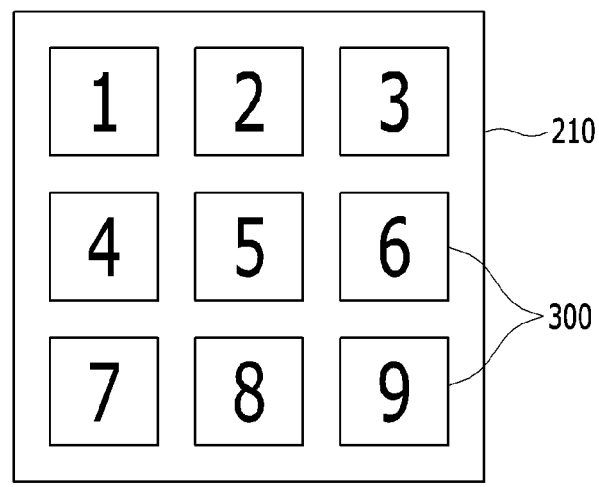
FIG. 4 is a schematic plan view of magnetic field generators in a welded portion quality determining system according to an exemplary embodiment of the present disclosure.

FIG. 4 is a schematic plan view of magnetic field generators in a welded portion quality determining system according to an exemplary embodiment of the present disclosure.

Referring to FIG. 4, the magnetic field generators 300 are arranged in the magnetic camera 210 at predetermined intervals in horizontal and vertical directions.

As illustrated in FIG. 4, the magnetic field generators 300 are arranged in a 3×3 arrangement. The method of arranging the magnetic field generators 300 and the number of magnetic field generators 300 may vary with design specification.

In FIG. 4, nine magnetic field generators 300 are operated sequentially. That is, a first magnetic field generator, a second magnetic field generator, a third magnetic field generator, a fourth magnetic field generator, a fifth magnetic field generator, a sixth magnetic field generator, a seventh magnetic field generator, an eighth magnetic field generator, and a ninth magnetic field generator are alternately operated in the order.

Figure 5:
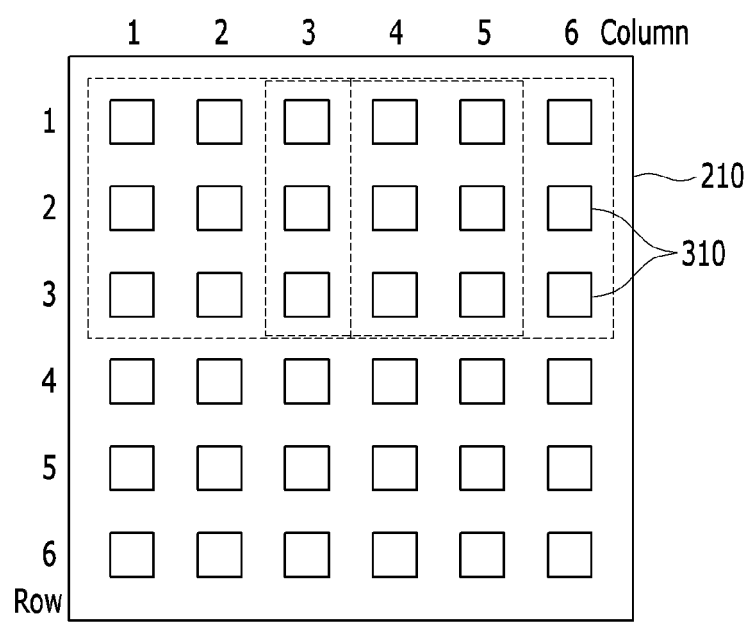
FIG. 5 is a schematic plan view of a magnetic pickup element in a welded portion quality determining system according to an exemplary embodiment of the present disclosure.

FIG. 5 is a schematic plan view of a magnetic pickup element in a welded portion quality determining system according to an exemplary embodiment of the present disclosure.

Referring to FIG. 5, the magnetic pickup devices 310 are arranged in the magnetic camera 210 at predetermined intervals in horizontal and vertical directions.

As illustrated in FIG. 5, the magnetic pickup devices 310 are arranged in a 6×6 arrangement. The method of arranging the magnetic field generators 300 and the number of magnetic field generators 300 may vary with design specification.

When the first magnetic field generator 300 in FIG. 4 is operated, the first, second, and third columns and first, second, and third rows of the magnetic pickup devices 310 in FIG. 5 are operated. When the second magnetic field generator 300 in FIG. 4 is operated, the second, third, fourth, and fifth columns and the first, second, and third rows of the magnetic pickup devices 310 in FIG. 5 are operated.

As described above, all of the magnetic field generators 300 and the magnetic pickup devices 310 are not operated but are sequentially operated so that maximum power and power consumption are reduced.

Figure 6:
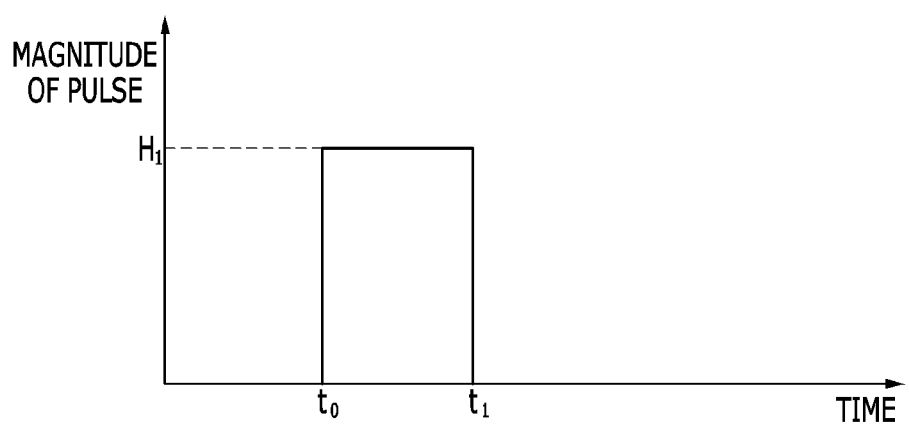
FIG. 6 is a graph illustrating a pulse applied from a welded portion quality determining system to magnetic field generators according to an exemplary embodiment of the present disclosure.

FIG. 6 is a graph illustrating a pulse applied from a welded portion quality determining system to magnetic field generators according to an exemplary embodiment of the present disclosure.

Referring to FIG. 6, a horizontal axis represents time, and a vertical axis represents a magnitude of a pulse. Here, the magnetic field is generated by the magnetic field generators 300 for a predetermined time, $t_0$ to $t_1$.

Figure 7:
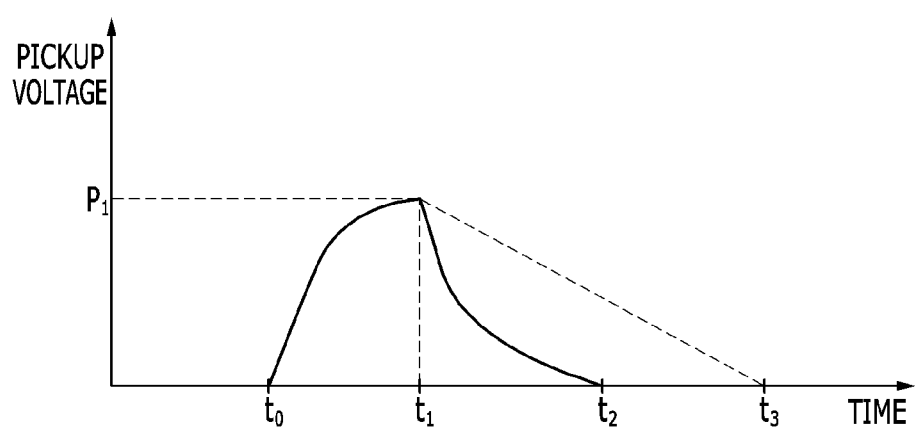
FIG. 7 is a graph illustrating a sensing signal of magnetic pickup devices in a welded portion quality determining system according to an exemplary embodiment of the present disclosure.

FIG. 7 is a graph illustrating a sensing signal of magnetic pickup devices in a welded portion quality determining system according to an exemplary embodiment of the present disclosure.

Referring to FIG. 7, a horizontal axis represents time, and a vertical axis represents a magnitude of a pickup voltage. Here, a pulse generated by the magnetic pickup devices 310 is increasing for a predetermined time, $t_0$ to $t_1$ and then is decreasing for a predetermined time, $t_1$ to $t_2$.

The pulse generated by the magnetic pickup devices 310 may be decreased for a predetermined time, $t_1$ to $t_3$ in accordance with a characteristic of the welded portion 250.

Figure 8:
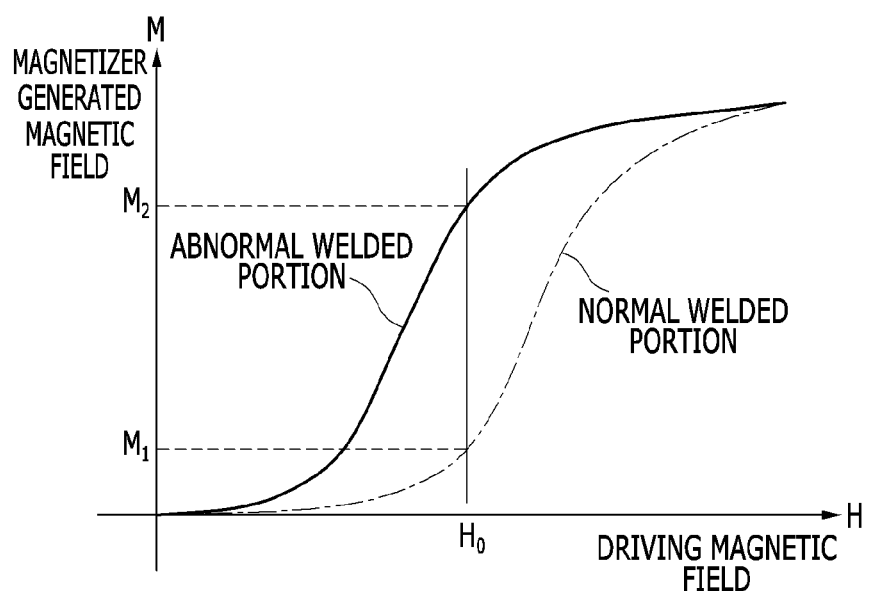
FIG. 8 is a graph illustrating a relationship between a driving magnetic field of magnetic field generators and a magnetizer generated magnetic field of magnetic pickup devices in a welded portion quality determining system according to an exemplary embodiment of the present disclosure.

FIG. 8 is a graph illustrating a relationship between a driving magnetic field of magnetic field generators and a magnetizer generated magnetic field of magnetic pickup devices in a welded portion quality determining system according to an exemplary embodiment of the present disclosure.

Referring to FIG. 8, a horizontal axis represents a magnitude of a driving magnetic field generated by the magnetic field generators 300, and a vertical axis represents a magnetizer generated magnetic field generated by the magnetized welded portion 250.

As illustrated in FIG. 8, a normal welded portion and an abnormal welded portion are magnetized, and characteristics of magnetizer generated magnetic fields generated by the magnetized normal welded portion and the magnetized abnormal welded portion are different from each other.

As described above, the magnetic field generators 300 generate the magnetic field at a predetermined level. The magnetic pickup devices 310 sense the magnetic field generated by the magnetized welded portion 250 and compare the sensed magnetic field pulse with predetermined data to easily determine a state of the welded portion 250.

While this disclosure has been described in connection with what is presently considered to be practical exemplary embodiments, it is to be understood that the disclosure is not limited to the disclosed embodiments. On the contrary, it is intended to cover various modifications and equivalent arrangements included within the spirit and scope of the appended claims.

What is claimed is:

1. A welded portion quality determining system, comprising:

a first plate and a second plate;

a welded portion defined at a point where the first plate and the second plate are welded to each other; and a magnetic camera comprising:
   magnetic field generators for generating a magnetic field to be supplied to the welded portion; and
   magnetic pickup devices for receiving the magnetic field generated by the magnetized welded portion to sense the received magnetic field, wherein one surface of the magnetic camera is disposed near one surface of the first plate or the second plate, and the magnetic field generators are sequentially operated in a horizontal or vertical direction in the order of arrangement to generate the magnetic field.

2. The welded portion quality determining system of claim 1, wherein the magnetic field generators are arranged at predetermined intervals in the horizontal and vertical directions.

3. The welded portion quality determining system of claim 1, wherein the magnetic pickup devices are arranged at predetermined intervals in the horizontal and vertical directions.

4. The welded portion quality determining system of claim 1, wherein a magnetic pickup device corresponding to an operated magnetic field generator among the magnetic field generators is operated to sense the magnetic field generated by the welded portion.

5. The welded portion quality determining system of claim 1, further comprising:
   a storage for storing first information on a magnetic field generated by a normal welded portion irradiated by a magnetic field to be magnetized and second information on a magnetic field generated by an abnormal welded portion irradiated by a magnetic field to be magnetized;
   an operator for comparing third information on the magnetic field generated by the magnetic pickup devices with the first and second information; and
   a controller for determining a state of the welded portion using an operation result from the operator.

\* \* \* \* \*